(12) United States Patent  
Biscup

(10) Patent No.: US 6,245,108 B1
(45) Date of Patent: Jun. 12, 2001

(54) SPINAL FUSION IMPLANT

(75) Inventor: Robert S. Biscup, Vermilion, OH (US)

(73) Assignee: Spineco, Westlake, OH (US)

( * ) Notice: Subject to any disclaimer, the term of this patent is extended or adjusted under 35 U.S.C. 154(b) by 0 days.

(21) Appl. No.: 09/494,645

(22) Filed: Jan. 31, 2000

Related U.S. Application Data

(60) Provisional application No. 60/121,705, filed on Feb. 25, 1999.

(51) Int. Cl.$^7$ ........................................ A61F 2/44
(52) U.S. Cl. ........................ 623/17.11; 623/17.16; 606/61
(58) Field of Search ............... 623/17.16, 17.11, 623/16.11; 606/60, 61, 53

(56) References Cited

U.S. PATENT DOCUMENTS

| | | |
|---|---|---|
| 4,349,921 | 9/1982 | Kuntz . |
| 4,834,757 | 5/1989 | Brantigan . |
| 4,878,915 | 11/1989 | Brantigan . |
| 4,961,740 | 10/1990 | Ray et al. . |
| 5,192,327 | 3/1993 | Brantigan . |
| 5,306,307 | 4/1994 | Senter et al. . |
| 5,425,772 | 6/1995 | Brantigan . |
| 5,607,424 | 3/1997 | Tropiano . |
| 5,609,635 * | 3/1997 | Michelson ............... 623/17.16 |
| 5,658,337 | 8/1997 | Kohrs et al. . |
| 5,766,252 | 6/1998 | Henry et al. . |
| 5,782,919 | 7/1998 | Zdeblick et al. . |
| 5,888,224 * | 3/1999 | Beckers et al. ............ 623/17.11 |
| 5,888,227 * | 3/1999 | Cottle ..................... 623/17.11 |
| 6,059,829 * | 5/2000 | Schlapfer et al. .......... 623/17.11 |
| 6,080,158 * | 6/2000 | Lin ................................ 606/61 |
| 6,113,638 * | 9/2000 | Williams et al. ........... 623/17.16 |

* cited by examiner

Primary Examiner—Pedro Philogene
(74) Attorney, Agent, or Firm—Vickers, Daniels & Young

(57) ABSTRACT

An improved prosthetic implant for forming a rigid structure between adjoining vertebrae in a spinal column. The prosthetic implant includes a cage having a top, bottom, front end, back end, first side and second side walls. The first side wall has an arcuate surface. The top and bottom wall include one or more ridges to engage a surface of an adjacent vertebrae. The top and bottom wall also include an opening to receive packing material such as medicine, human tissue and the like. The top and bottom walls also incline simultaneously in two directions.

59 Claims, 4 Drawing Sheets

FIG. 5
FIG. 6
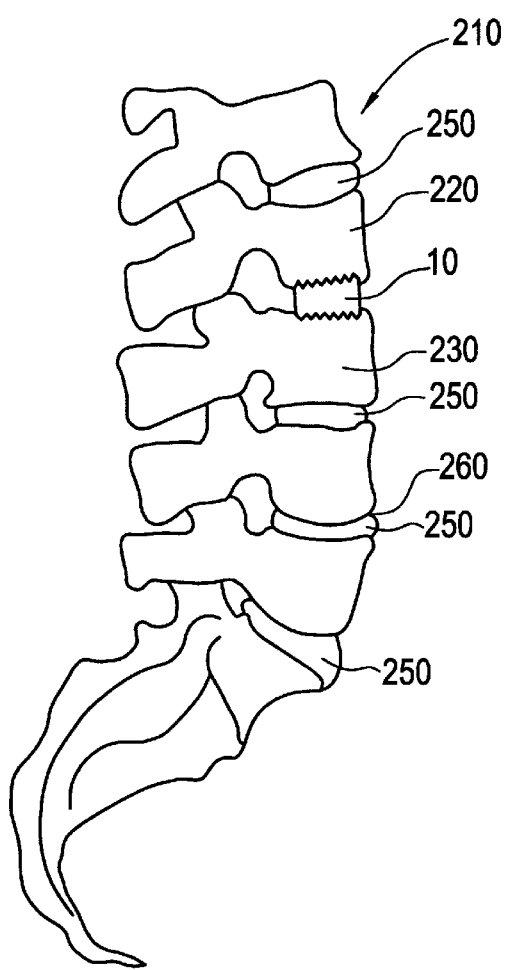
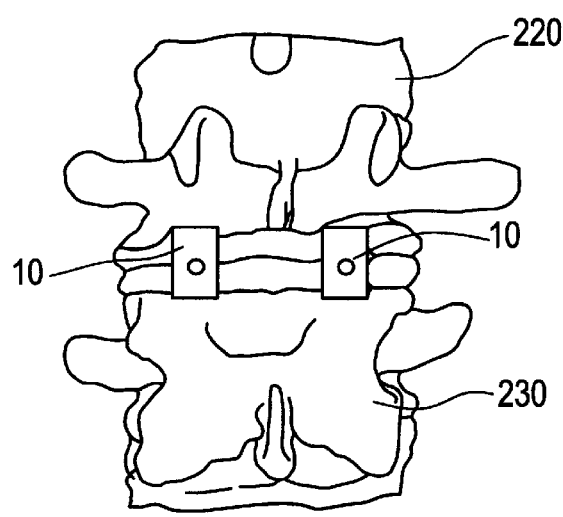

SPINAL FUSION IMPLANT

This application claims priority on my co-pending U.S. Provisional Application Ser. No. 60/121,705, filed Feb. 25, 1999 entitled "Spinal Fusion Implant."

The present invention pertains to prosthetic implants and more particularly to inner body spinal prosthetic implants to fuse two or more vertebrae together.

INCORPORATION BY REFERENCE

U.S. Provisional Application Ser. No. 60/121,705, filed Feb. 25, 1999 entitled "Spinal Fusion Implant" is incorporated by reference.

BACKGROUND OF THE INVENTION

The human spine is made up of a column of thirty-three bones and their adjoining structures. The vertebrae near the head are known as the presacral vertebrae which are separate bones capable of individual movement. The bodies of these vertebrae are connected by anterior and posterior ligaments and by disks of fibrocartilage generally known as intervertebral disks. These disks are positioned between opposite faces of adjacent vertebral bodies. This column of vertebrae and intervertebral disks form a central axis that supports the head and torso. These vertebrae also enclose an opening through which the spinal cord passes therebetween.

The presacral vertebrae are normally held in position to one another by the intervertebral disks, ligaments and musculature of the body. These vertebrae move relative to adjacent vertebrae thus permitting the head to be turned relative the body and providing a wide range of flexibility to the spine.

One of the most costly health problems to society involves back pain and pathology of the spine. These problems can affect individuals of all ages and can result in great suffering to victims. Back pain can be caused by several factors such as congenital deformities, traumatic injuries, degenerative changes to the spine and the like. Such changes can cause painful excessive motion, or collapse of a motion segment resulting in the contraction of the spinal canal and compresses the neural structures causing debilitating pain, paralysis or both which in turn can result in nerve root compression or spinal stenosis.

Nerve conduction disorders can also be associated with invertible disks or the vertebrae themselves. One such condition is herniation of the intervertebral disk, in which a small amount of tissue protrudes from the sides of the disk into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniations of the intervertebral disk, one such surgical procedure is intervertebral diskectomy. In this procedure, the involved vertebrae are exposed and the intervertebral disk is removed, thus removing the offending tissue, or providing access for the removal of the bone osteophytes. A second procedure, termed a spinal fusion, may then be required to fix the vertebrae together to prevent movement and maintain a space originally occupied by the intervertebral disk. Although this procedure may result in some minor loss and flexibility in the spine, due to the relatively large number of vertebrae, the minor loss of mobility is typically acceptable.

During a spinal fusion following a diskectomy, a prosthetic implant or spinal implant is inserted into the intervertebral space. This prosthetic implant is often a bone graft removed from another portion of the patient's body, termed an autograph. The use of bone taken from the patient's body has the important advantage of avoiding rejection of the implant, but has several shortcomings. There is always a risk in opening a second surgical site in obtaining the implant, which can lead to infection or pain for the patient, and the site of the implant is weakened by the removal of bony material. The bone implant may not be perfectly shaped and placed, leading to slippage or absorption of the implant, or failure of the implant to fuse with the vertebrae.

Other options for a graft source of the implant are bone removed from cadavers, termed allograft, or from other species, termed a xenograft. In these cases while there is the benefit of not having a second surgical site as a possible source of infection or pain, there is increased difficulty of the graft rejection and the risk of transmitting communicable diseases.

An alternative approach is using a bone graft or to use a manufactured implant made of a synthetic material that is biologically compatible with the body and the vertebrae. Several compositions and geometries of such implants have been utilized, ranging from simple blocks of material to carefully shaped implants, with varying success.

There has been an extensive number of attempts in developing an acceptable prosthetic implant that can be used to replace an intervertebral disk and yet maintain the stability of the intervertebral disk spaced between adjacent vertebrae, at least until complete arthrodesis is achieved. These prosthetic implants have taken many forms. While many types of synthetic prosthetic devices have been proposed, the success ratio has been low and the surgical procedures have been complicated and often traumatic to the patient.

One of the more prevailing designs of these prosthetic implants takes form of a cylindrical implant. These types of prosthetic implants are represented by Brantigan U.S. Pat. No. 4,878,915 and Ray U.S. Pat. No. 4,961,740. In these cylindrical implants, the exterior portion of the cylinder can be threaded to facilitate insertion of the prosthetic device. Some of these prosthetic implants are designed to be pounded into the intervertebral disk space and the vertebral end plates. These types of devices are represented in Brantigan U.S. Pat. No. 4,834,757 and Brantigan U.S. Pat. No. 5,192,327. The Brantigan and Ray patents all disclose prosthetic implants wherein the transverse cross-section of the implant is constant throughout the length of the implant and is typically in the form of a right circular cylinder.

Other prosthetic implants have been developed that do not have a constant cross-section. For instance, the patent to McKinna U.S. Pat. No. 4,714,469 shows a hemispherical implant with elongated protuberances that project into the vertebral end plate. The implant of Bagby U.S. Pat. No. 4,934,848 is in the form of a sphere which is positioned between the centrums of the adjacent vertebrae.

The various prosthetic implants can be generally divided into two basic categories, namely, solid implants and implants that are designed to encourage bone ingrowth. Solid implants are represented by U.S. Pat. Nos. 4,878,915 and 4,349,921. The remaining patents discussed above include some aspect that permits bone to grow across the implant. It has been found that devices which promote natural bone ingrowth achieve a more rapid and stable arthrodesis. These implants are typically filled with autologous bone prior to insertion into the intervertebral disk space. These implants typically include apertures which communicate with openings in the implant, thereby providing a path for tissue growth between the vertebral end plate and the bone or bone substitute within the implant. In preparing the intervertebral disk space for a prosthetic implant, the end plates of the vertebrae are preferably reduced to bleeding bone to facilitate tissue growth within the implant.

A number of difficulties still remain with the many prosthetic implants currently available. While it is recognized that hollow implants which permit bone ingrowth in the bone or bone substitute within the implant is an optimum technique for achieving fusion, most of these devices have difficulty achieving this fusion, at least without the aid of some additional stabilizing device, such as a rod or plate. Moreover, some of these devices are not structurally strong enough to support the heavy loads applied at the most frequently fused vertebral levels, mainly those in the lower lumbar spine.

There has been a need for providing a prosthetic implant that optimizes the bone ingrowth capabilities and strong enough to support the vertebrae until arthrodesis occurs. There is a further need for such an implant that is capable of maintaining or restoring the normal spinal anatomy at the instrumented segment. There is also a need for an implant that exhibits reduced slippage when inserted between vertebrae and diminishes the occurrence of nerve pinching.

SUMMARY OF THE INVENTION

The present invention pertains to an improved implant and more particularly to an improved prosthetic implant used to facilitate in the fusion of two or more vertebrae.

In accordance with the principal feature of the present invention, there is provided a prosthetic implant that is formed of a biologically compatible material for use in humans. The prosthetic implant is shaped and sized for insertion between two vertebrae. In one specific embodiment, the prosthetic implant is designed to be placed in the intervertebral disk space that was formerly occupied by an intervertebral disk. The intervertebral disk is partially or completely removed prior to insertion of the prosthetic implant between the vertebrae. In one specific embodiment, the shape and size of the cage is selected to have an anatomically correct shape. In another embodiment, the prosthetic implant is shaped to increase the area of contact with the vertebrae and/or to closely emulate the region formerly occupied by the intervertebral disk. In still another embodiment, the prosthetic implant is designed to be readily inserted by established surgical procedures, with minimal chances of surgical difficulty. In yet another embodiment, the geometry of the implant ensures proper load bearing, desired load bearing and support through the fused vertebrae minimizing the likelihood of the prosthetic implant dislocating relative to the vertebrae either during surgery or during the post operative fusing process.

In accordance with another aspect of the present invention, there is provided a prosthetic implant which includes a cage having a top wall, a bottom wall, a front end wall, a back end wall, a first side wall, and a second side wall. In one embodiment, the cage is made of a material that is inert or biologically compatible with the vertebrae. The material of the cage includes, but is not limited to, bone, stainless steal, titanium, chrome, cobalt, polycarbonate, polypropelene, polyethylene, polymethylmethacrylate, polysolfone types filled with glass and/or carbon fibers, and various types of carbon and fiber reinforced polymers. In accordance with another embodiment, the cage is designed to maintain a tension load of about ten to forty pounds and more preferably about fifteen to thirty-five pounds on the disk tissue. This tension load facilitates in maintaining the cage in position between the vertebrae and accelerates bone ingrowth between the vertebrae. In still another embodiment, the cage is made of a material which closely approximates the elasticity of the vertebra. In still yet another embodiment, the cage is coated with and/or made up of material which is radiolucent to enhance the visibility of the implant when exposed to X-rays.

In accordance with still another aspect of the present invention, the first side wall and second side wall of the cage of the prosthetic implant extends substantially along the longitudinal axis of the cage and wherein the two side walls are configured to enhance the stability of the cage within the intervertebral disk space. In one embodiment, the first and/or second side wall is at least partially arcuate. In another embodiment, the first and second side wall have different face configurations. In one specific embodiment, the first side includes an arcuate surface and the second side has a substantially flat or planar surface. In one specific embodiment, the first side wall has a substantially uniform arcuate surface. In another specific embodiment, the actuate surface has a radius of curvature of about 2 to 30 degrees. In cage configurations having an arcuate first side wall surface, the cage is positioned in the intervertebral disk space such that the substantially flat or planar surface of the second side is positioned closely adjacent to the spinal cord and the first side is positioned adjacent the peripheral edge of the intervertebral disk space. Prosthetic implant cages having an arcuate or curvilinear side wall have been found to more closely conform to the surfaces with the intervertebral disk space thereby resulting in a higher degree of success for fusing together two vertebrae. The different side configurations of the cage also function as a visual aid to ensure that the cage is properly oriented between two vertebrae.

In accordance with yet another aspect of the present invention, the cage of the prosthetic implant includes a top wall and/or bottom wall having at least one rigid surface adapted to engage the underside surface of a vertebrae within the intervertebral disk space. The ridge is designed to secure or bite into the vertebrae surface. In one embodiment, the top wall includes a plurality of ridged surfaces. In another embodiment, the bottom wall includes a plurality of ridged surfaces. The ridged surfaces on the top and/or bottom wall can have a number of configurations. In one specific embodiment, the ridges have diamond shaped surfaces, thereby functioning similar to teeth-like structures. In another specific embodiment, the ridge is a uniform structure extending over the lateral and/or longitudinal surface of the top and/or bottom wall. In another embodiment, the ridges are positioned on the top end and/or bottom wall and are spaced from the outer peripheral edge of the bottom and/or top wall. In still another embodiment, the top and bottom wall have similar ridge configurations and a similar number of ridges; however, it can be appreciated that the top and bottom wall can have different numbers and/or different configurations of ridges. In still yet another embodiment, the ridges in the top and/or bottom wall of the cage anchor the cage in between the vertebrae and provide channels for bone ingrowth which facilitates in the fusion of the vertebrae.

In accordance with still yet another aspect of the present invention, the cage of the prosthetic implant includes one or more openings in one or more of the walls of the cage. In one embodiment, the openings are designed to receive materials which facilitate in the fusion of the vertebrae, facilitate in the positioning of the cage between the vertebrae, and/or secure the cage in place within the intervertebral disk space. In one specific embodiment, one or more of the openings are designed to receive a packing material which facilitates in the formation of a graft between two vertebrae. Such packing material can include, but is not limited to, medicine, human tissue, animal tissue, synthetic tissue, human cells, animal cells, synthetic cells, and the like. In another specific embodiment, the cage includes a plurality of openings to allow blood supply to grow from the sides of the cage to the vertebrae between the cage. In still another specific embodiment, one or more openings in the cage are filled with a packing material which includes one or more components that are selected to grow out of the openings of the cage radially, longitudinally and/or vertically from the cage and grow into the bone tissue of the adjoining adjacent vertebrae. In still another specific embodiment, one or more openings are filled with bone material or a synthetic material, with or without a bone activating matter such as hydroxyapatite bone or phallic protein, bone growth factor, or cartilage activation factor. In yet another embodiment, the top and/or bottom wall of the cage have an opening which communicates with an internal cavity of the cage. In still yet another embodiment, the top and bottom walls include at least one opening that are substantially the same shape and size. In accordance with another embodiment, the first side wall, second side wall, front end wall and/or back end wall include at least one opening adapted to receive an instrument for guiding and/or inserting the cage between the vertebrae of the spine by an anterior, posterior, lateral and/or latroscopic approach into the spinal column. The openings allow a surgeon to select which approach is best for inserting the prosthetic implant in the intervertebral disk space. In one specific embodiment, the instrument opening includes a securing mechanism, such as, but not limited to, a thread, in the opening to secure the instrument within the opening.

In accordance with another aspect of the present invention, at least one or more edges of the cage are rounded off so as not to be sharp. The rounding off of the edges reduces and/or eliminates pinching of the nerve leading from the spinal cord which can result in pain, damage or paralysis to the individual. The rounded edges avoid or minimize nerve pressure that can be exerted on the nerves interverte-brally exiting the spinal cord. The one or more rounded off edges also facilitates with the insertion of the cage within the intervertebral disk space. In one specific embodiment, the lateral edges of the cage are rounded off. In another specific embodiment, all the edges of the cage are rounded off.

In accordance with still another aspect of the present invention, the top wall and/or bottom wall are at least partially inclined along the longitudinal axis of the cage. In one embodiment, the top wall and/or bottom wall are uniformly inclined from the back end wall to the front end wall. In one specific embodiment, the back end wall is higher than the front end wall. In another specific embodiment, the angle of inclination of the top and/or bottom wall is about 0.5 to 15 degrees and preferably about 1 to 10 degrees and more preferably about 3 to 8 degrees. The inclination of the top and/or bottom wall of the cage facilitates in the ease of insertion into the vertebrae column and/or provides a better fit for the cage within the intervertebral disk space since the inclination better matches the anatomical shape of the space between the vertebrae of the spinal column. In accordance with another embodiment, the inclined top and/or bottom wall of the cage accommodate the positioning of the cage between two vertebrae of the spinal column and the ridges on the top and/or bottom wall of the cage are adapted to contact the surfaces of the vertebrae bone and secure the cage in position between the vertebrae until the fusion of the vertebrae is complete.

In accordance with yet another aspect of the present invention, the top wall and/or bottom wall are at least partially inclined between the first and second side wall of the cage. In one embodiment, the top wall and/or bottom wall are uniformly inclined from the first and second side wall. In one specific embodiment, the second side wall is higher than the first side wall. In another specific embodiment, the angle of inclination of the top and/or bottom wall is about 0.5 to 15 degrees and preferably about 1 to 10 degrees and more preferably about 3 to 8 degrees. The inclination of the top and/or bottom wall of the cage facilitates in the ease of insertion into the vertebrae column and/or provides a better fit for the cage within the intervertebral disk space since the inclination better matches the anatomical shape of the space between the vertebrae of the spinal column.

In accordance with another aspect of the present invention, a pair of cages are used to support and/or fuse two vertebrae in the spinal column. In one embodiment, the cages are positioned in a side by side relation to form a rigid transverse strut between adjacent vertebrae.

It is an object of the present invention to provide an improved prosthetic implant for insertion between two vertebrae.

It is another object of the present invention is to provide a prosthetic implant which better emulates the space between the vertebrae.

Yet another object of the present invention to provide a prosthetic implant which includes one or more ridges to help secure the prosthetic implant in position between the vertebrae.

It is yet another object of the present invention to provide a prosthetic implant which is used in a side by side relation to form a rigid transverse strut between adjacent vertebrae.

It is still yet another object of the present invention to provide a prosthetic implant which provides improved spinal support fixation and methodology which provides stability between adjacent vertebrae and the shape will facilitate in securing the prosthetic implant between the vertebrae.

Another object of the present invention is to provide an apparatus which will aid in the positioning of the prosthetic implant between the vertebrae.

Still yet another object of the present invention is to provide a prosthetic implant which has one or more openings that can receive packing material to facilitate in the fusion of two adjacently positioned vertebrae.

A further object of the present invention is to provide a prosthetic implant which can be easily and efficiently positioned between two vertebrae and which reduces the failure rate of prosthetic implants between the vertebrae.

It is another object of the present invention to provide a prosthetic implant which includes one or more sloped surfaces to facilitate in the insertion of the prosthetic implant between the adjacently positioned vertebrae and to better match the shape of the prosthetic implant to the space between the adjacently positioned vertebrae.

It is still another object of the present invention to provide a prosthetic implant which includes surfaces that reduce pinching with the spinal cord and other body parts closely adjacent to the prosthetic implant.

It is another object of the present invention to provide a prosthetic implant that is made of a biologically compatible material.

It is another object of the present invention to provide a prosthetic implant that is made of and/or coated with a radiolucent material.

It is another object of the present invention to provide a prosthetic implant that is made of a material which closely approximates the elasticity of the vertebra.

These and other objects of the invention will become apparent to those skilled in the art upon reading and understanding the following detailed description of preferred embodiments taken together with the drawings.

BRIEF DESCRIPTION OF THE DRAWINGS

The invention may take physical form in certain parts and arrangement of parts, preferred embodiments of which will be described in detail and illustrated in the accompanying drawings which form a part hereof and wherein:

FIG. 5 is a side elevation view of a spinal column which includes the prosthetic implant of the present invention positioned between two adjacently positioned vertebrae; and FIG. 6 is a posterior elevation view of a portion of FIG. 5 illustrating two adjacently positioned prosthetic implants positioned between two spinal vertebrae.

DESCRIPTION OF THE PREFERRED EMBODIMENT

Figure 1:
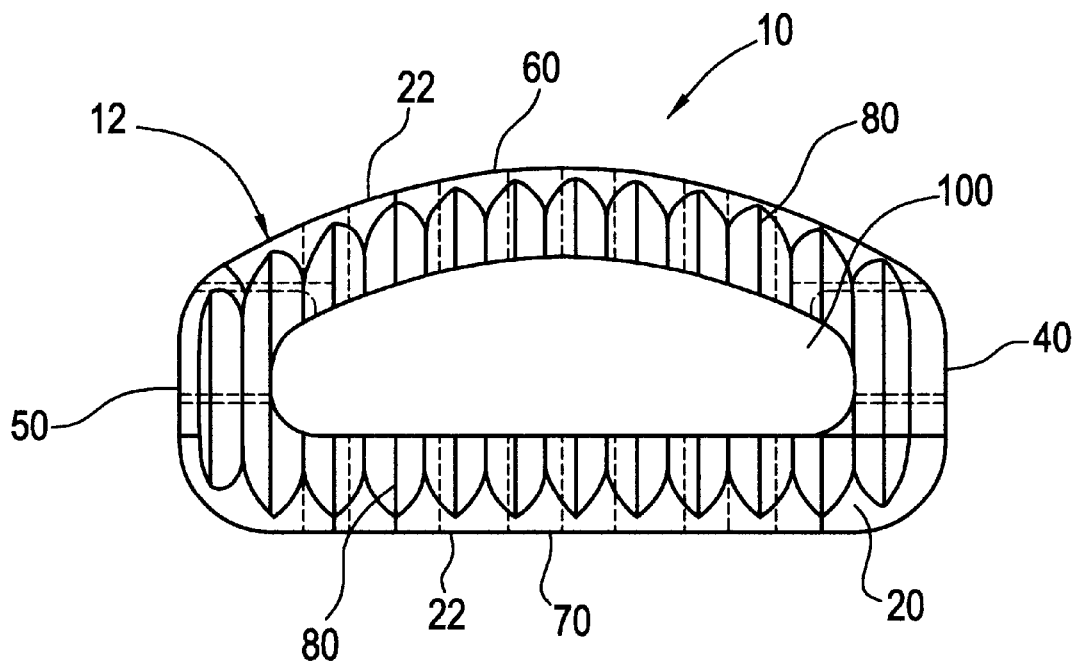
FIG. 1 is a top plan view of the prosthetic implant of the present invention.
Figure 2:
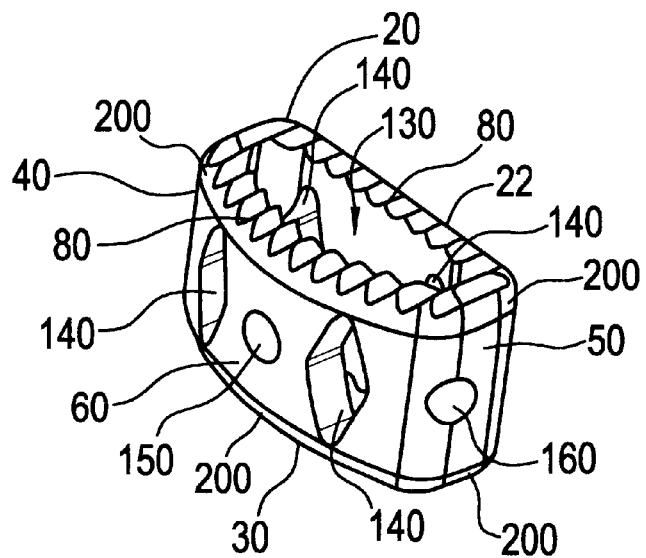
FIG. 2 is a prospective view of the prosthetic implant of the present invention.
Figure 3:
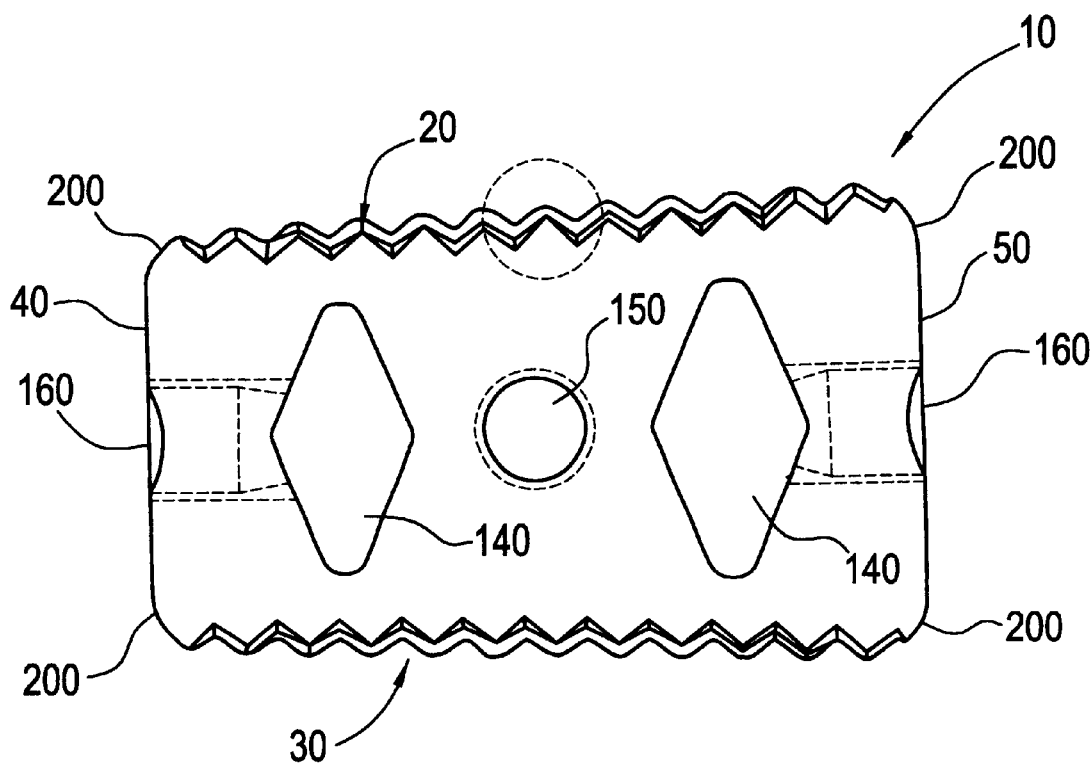
FIG. 3 is a side elevation view of the prosthetic implant of the present invention.

Referring to the drawings, wherein the showings are for the purpose of illustrating the preferred embodiment of the invention only and not for the purpose of limiting same, FIGS. 1–3 illustrate a prosthetic device or implant 10 which is designed to be inserted in an intervertebral disk space between two vertebrae of the spinal column. Prosthetic implant 10 is illustrated as being a cage-like structure 12 having a top wall 20, a bottom wall 30, a front end wall 40, a back end wall 50, a first side wall 60, and a back side wall 70. As best illustrated in FIGS. 1 and 2, the top wall 20 includes a plurality of ridge structures 80 which are positioned along the longitudinal length of prosthetic implant 10. As illustrated in FIG. 3, ridge structures 80 are also included on bottom wall 30. The ridge structures can be cut into the top and bottom walls and/or be formed by a molding process. The ridge structures are designed to bite into and/or readily form a rigid contact with the underside surface of the vertebrae so as to secure the prosthetic implant between the vertebrae and reduce the movement of the prosthetic implant of the vertebrae after the prosthetic implant has been properly positioned between the vertebrae.

Figure 3A:
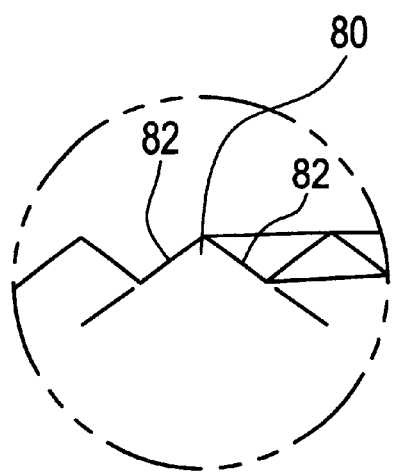
FIG. 3A is an enlarged view of an alternate ridge configuration in the top wall of the prosthetic implant of FIG. 3.

Referring to FIGS. 1 and 2, ridge structures 80 are shown to be spaced from the peripheral edge 22 of top wall 20. This same spacing of the ridges also exists on the bottom wall. Top wall 20 is also shown to include an opening 100. Many different ridge configurations can be used on the top and bottom walls of cage 10. Two preferable configurations are illustrated in FIGS. 1 and 3A. In FIG. 1, the ridge structures are groove type ridges that are oriented along the lateral axis of cage 12. The ridge structures have two sides that are similar in length. In one arrangement, the height of the ridge structure from valley to peak is about 0.01 to 0.05 inch, and the spacing between ridge peaks is about 0.01 to 0.12 inch. As can be appreciated, these dimensions of the ridge structures can be modified for use in a particular application.

Referring now to FIG. 3A, an alternative configuration of the ridge structure is shown. Ridge structures 80 are generally diamond shaped structures wherein each ridge structure has four walls. The walls 82 of the diamond shaped ridge structure are generally the same size and shape. In one arrangement, the height of the ridge structure from valley to peak is about 0.01 to 0.05 inch, and the spacing between ridge peaks is about 0.01 to 0.12 inch. As can be appreciated, these dimensions of the ridge structures can be modified for use in a particular application.

The ridge structures can be oriented in the top and/or bottom wall to facilitate in the stacking or two or more prosthetic implants.

Figure 4:
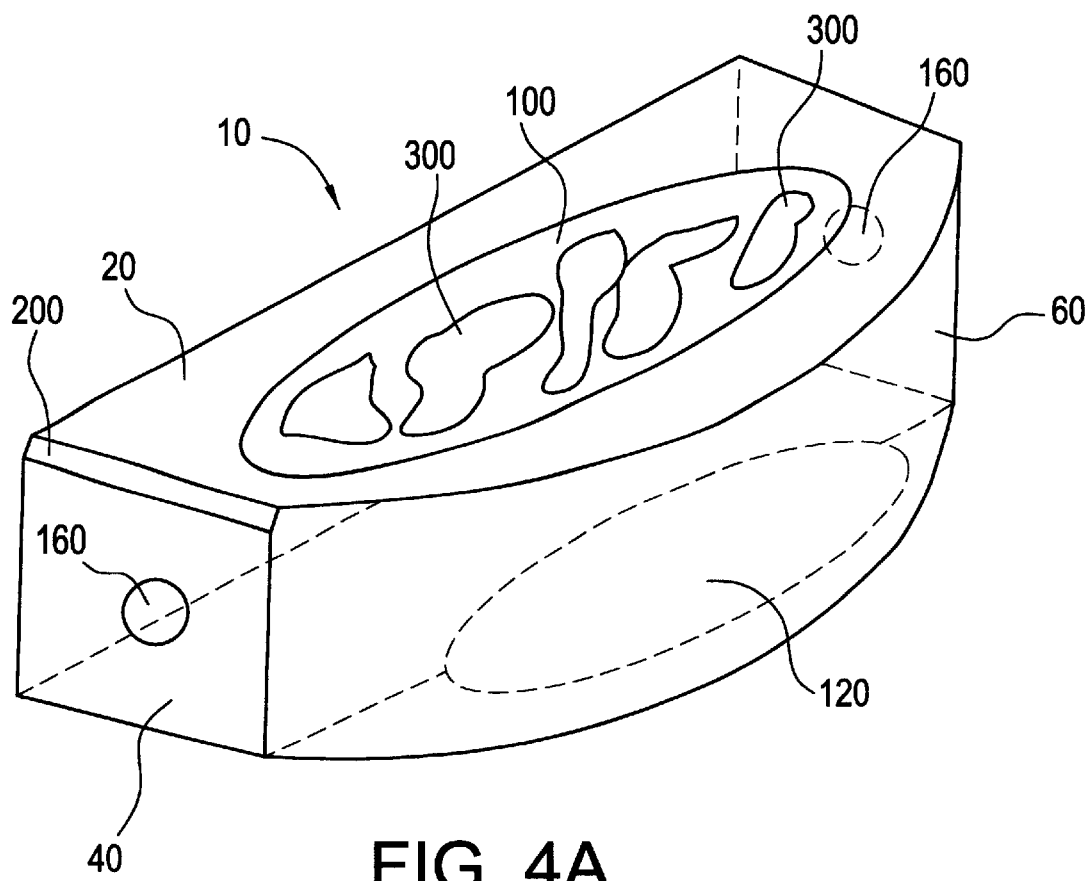
FIG. 4 is prospective view of another embodiment of the prosthetic implant of the present invention which illustrates the dual sloping of the top and bottom walls of the prosthetic implant.

Referring to FIGS. 1 and 4, the top and bottom wall of cage 12 includes an openings 100, 120. Openings 100, 120 are illustrated as being semi-oval shaped; however, other opening shapes can be used. The size of the opening is selected so packing materials 300 can be inserted in the openings. In one desired arrangement, the size of openings 100, 120 are maximized to increase the volume of packing materials that can be inserted into the cage without adversely affecting the structural integrity of the cage. As illustrated in FIGS. 1 and 4, openings 100 and 120 have a similar shape and size; however, other shapes and sizes of the openings can be used. The openings are shown to have a peripheral edge spaced at a generally uniform distance from the peripheral edge of the top and bottom wall. In one desired arrangement, the spacing of the peripheral edge of the opening from the peripheral edge of the top and bottom walls is about 0.05 to 0.25 inch; however, other spacings can be used based upon the material and size of the cage.

Referring now to FIGS. 1, 2 and 4, cage 12 includes a cavity 130. Cavity 130 is shown to be in communication with opening 100, 120 in the top and bottom walls of cage 12. The cavity is designed to increase the amount of packing material that can be inserted in the cage. The packing material 300 includes, but is not limited to, medicine, tissue, cells, and the like. In one desired arrangement, the packing material is selected to facilitate in the growth of bone between the two vertebrae in which the prosthetic implant is inserted therebetween.

Referring now to FIG. 2, the first side wall 60 has an arcuate or curvilinear shape along the longitudinal length of the wall. The arcuate shape of the first side wall is selected to more closely anatomically match the intervertebral disk space. Second side wall 70 is illustrated as having a substantially straight or planar face. When prosthetic implant 10 is positioned in the intervertebral disk space, second side wall 70 is positioned closely adjacent to the spinal cord and first side wall 60 is positioned adjacent the outer edge of the vertebrae. The curvilinear first side wall and the substantially planar or straight second side wall are designed to more closely match the intervertebral disk space and to increase the surface area of contact with the vertebrae to assist in reducing slippage and to increase the success rate of the fusion between two vertebrae. As can be appreciated, the shape of the arcuate surface of first side wall 60 can be adjusted depending on the vertebrae in which the prosthetic implant is to be inserted therebetween. As also can be appreciated, second side wall 70 may also be shaped to include non-planar surfaces to further facilitate in the maximization of contact of the surfaces of the prosthetic implant to the underside surfaces of the vertebrae. In one desired embodiment, the planar second side wall has a length of about 0.5 to 1.2 inch and a height of about 0.2 to 0.8 inch. In another desired embodiment, the radius of curvature of the first side wall is about 0.3 to 0.9 inch and a height of about 0.1 to 0.75 inch. As can be appreciated, the size and configuration of the side wall can take on other dimensions and configurations depending on the use of the prosthetic implant.

Referring again to FIG. 2, first side wall 60 and second side wall 70 include openings 140 which communicate with inner cavity 130. As with openings 100 and 120 in the top and bottom walls, openings 140 are designed to receiving packing material 300 and to allow for blood flow between the packing material within the cavity 130 and the surrounding regions of the vertebrae. Openings 140 are illustrated as being diamond shaped; however, other shapes can be used. The side walls are also illustrated as each including two openings 140; however, more or less openings can be included in the side walls. In one desire embodiment, oval or diamond shaped openings are used in the side walls to maximize the opening size without adversely affecting the structural integrity of the cage.

Referring again to FIG. 2, the side walls include an instrument opening 150 which is designed to receive an instrument to enable the prosthetic device to be inserted in the intervertebral disk space in number of different approaches. In one desired embodiment, the prosthetic implant includes a plurality of instrument opening 150 to enable the prosthetic implant to be inserted in the intervertebral disk space from an anterior, posterior, lateral, and/or lateralscopic approach to the vertebrae. In another desired embodiment, the instrument opening 150 is a threaded opening which receives a threaded instrument. The threaded opening allows an instrument to be simply secured to and/or removed from the prosthetic implant 10. The instrument opening 150 can also be used to secure pedicle screws to the prosthetic implant so as to facilitate attachment to a rod or plate stabilization system to the prosthetic implant.

Referring now to FIGS. 2 and 4, front and back end walls 40, 50 include an instrument opening 160. The configuration and function of instrument opening 160 is the same as instrument opening 150 in the first and second walls of cage 12.

Referring now to FIG. 2, the peripheral edges of the walls of the cage are rounded off or contoured. The rounded off edges 200 are designed to minimize or eliminate sharp edges on the cage to reduce and/or eliminate pinching of the nerves, and to facilitate in the positioning of the cage in the intervertebral disk space.

Referring now to FIG. 3, the top and bottom walls of the cage are inclined. Top wall 20 and bottom wall 30 are shown to slope downwardly from back end wall 50 to front end wall 40. The angle of incline is shown to be generally uniform throughout the longitudinal length of the prosthetic implant. The degree of inclination of both the top wall and bottom wall of the prosthetic implant is substantially the same. Due to the sloping surfaces of the top and bottom wall, the back end wall 50 is shown to have a higher height than front wall 40. In one desired embodiment, the height of the back end wall is about 0.2 to 0.8 inch, the height of the front side wall is about 0.1 to 0.75 inch, and the angle of slope of the top and bottom wall from the back to front end wall is about 0.5 to 20 degrees.

Figure 4A:
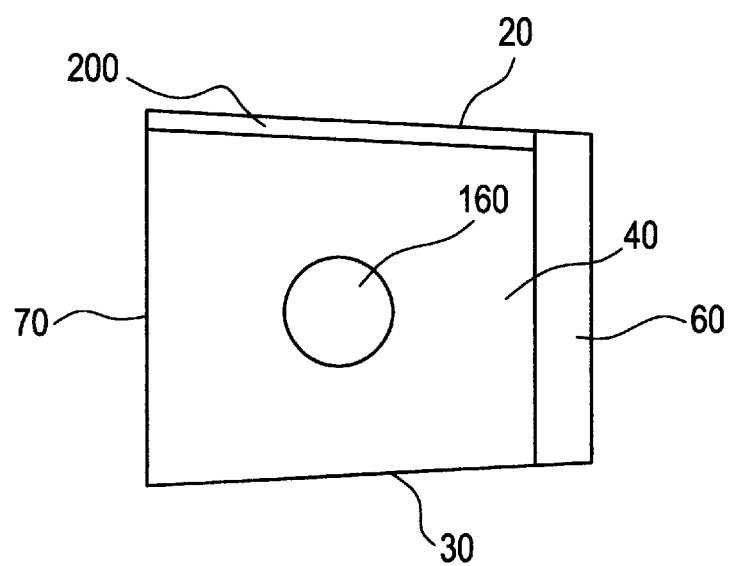
FIG. 4A is a rear end view of the prosthetic implant in FIG. 4.

Referring now to FIGS. 3, 4 and 4A, the top and bottom walls of cage 12 are inclined from the second side wall to the first side wall. In one desired embodiment, the degree of inclination of the top and bottom wall from the second side wall to the first side wall is substantially uniform. Due to the incline of the top and bottom wall, the second side wall has a higher height than the first side wall. In another desired embodiment, the angle of slope of the top and bottom wall from the back to front end wall is about 0.5 to 20 degrees.

Referring now to FIGS. 5 and 6, the lower portion of the human vertebrae column 210 is illustrated. FIG. 5 illustrates five lower vertebrae of the spinal column. Vertebrae 220 and 230 are separated by and supported on the prosthetic implant 10 of the present invention. The remaining vertebrae are illustrated as being supported on and separately by intervertebral disk 250 which maintains a space 260 between the adjoining vertebrae. The damaged portions of intervertebral disk 250 have been removed from between vertebrae 220 and 230 prior to prosthetic implant 10 being inserted therebetween. As shown in FIG. 6, two prosthetic implants 10 are positioned side by side between vertebrae 220 and 230.

As an overview of one embodiment of the invention, the prosthetic implant is a solid structure of a cage having one or more cavities. The implant is to be inserted into the vertebral column during surgery to provide load bearing support for the vertebrae in the vertebral column. The implant is shaped to provide a slope laterally so that the medium aspect closest to the spinal column is higher than the lateral aspect. The implant has one or more openings in the cage to allow for packing materials not rejected by the human body. These packing materials include, but are not limited to, autologous bone, donated human bone material, other mammalian materials, and/or other natural or artificial materials. The cage is sloped from the anterior to the posterior. The cage has rounded edges to reduce spinal pinching. The top and bottom walls of the cage include ridges or grooves that are carved into the top and bottom walls to facilitate in the fixation and anchoring of the cage between two vertebrae. The ridges can have several configurations, one being a cross hatched or teeth design which form diamond bumps or pyramids. The cage has one or more arcuate or curvilinear sides that forms an ovoid shaped cage or a double domed disk configuration.

In the most common applications, two prosthetic implants will be utilized and inserted in the intervertebral disk space, one on each side of the lateral sides of the spinal column. The prosthetic devices will replace a damaged or injured disk that is partially or wholly removed during a surgical procedure. During the surgical procedure, the implants will be inserted and fixed in a location to avoid intrusion into the spinal cord area while at the same time avoiding extending outside the vertebral column. This placement of the prosthetic implants is optimized by utilizing the prosthetic implant of the present invention.

Some advantages and improvements of the prosthetic implant over prior art implants are:

The comers of the implant are rounded.

The top wall of the implant slopes from one side wall to another side wall.

The bottom wall of the implant slopes from one side wall to another side wall.

The top wall of the implant slopes from one end wall to another end wall.

The bottom wall of the implant slopes from one end wall to another end wall.

The implant includes larger and/or more openings to facilitate in the packing of the implant with bone and/or bone growth promoters.

The top and/or bottom surfaces of the implant include ridged surfaces having a diamond shaped design for better bone anchoring.

The walls of the implant include one or more threaded holes to enable the implant to be inserted from the anterior, posterior, lateral, or laproscopic approach during surgery.

The implant is designed to receive interference screws and/or stints used to inhibit the migration of the implant within the intervertebral disk space.

The implant can be made of a variety of materials such as chopped carbon fiber/polymer, other polymers, various metals, memory metals, ceramics, bone, bio-resorbables, and/or composites.

The implant can be made of a memory metal that can be expanded after being inserted in the intervertebral disk space. The cage can be designed to be expanded "in vivo."

The implant can be used with a modular component that can be attached and assembled between two implants to create a construct (ALIF type) cage.

The implant can be stacked upon one another to form a corpectomy cage having various shapes and sizes.

The implant is designed to accept insertion of machine-threaded pedicle screws so as to facilitate attachment to a rod or plate stabilization system.

The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations in so far as they come within the scope of the appended claims.

I claim:

1. A prosthetic implant to form a rigid structure between adjoining vertebrae in a spinal column comprising a cage defined by top, bottom, front end, back end, first side and second side walls, said first and second side walls extending substantially along a longitudinal axis of said cage, said front and back end walls having a width less than the length of said first side and said second side walls, said top wall and said bottom wall positionable between and engageable with a surface of an adjacent vertebrae, said first side wall having an arcuate surface, said second side wall being a substantially planar surface, said top wall being inclined downwardly from said back end wall to said front end wall such that at least a portion of said back end wall has a height greater than a height of at least a portion of said front end wall.

2. The prosthetic implant as defined in claim 1, wherein said top wall includes at least one ridge to engage a surface of an adjacent vertebrae.

3. The prosthetic implant as defined in claim 1, wherein said bottom wall includes at least one ridge to engage a surface of an adjacent vertebrae.

4. The prosthetic implant as defined in claim 2, wherein said top wall includes a plurality of ridges.

5. The prosthetic implant as defined in claim 2, wherein at least one of said ridge includes a plurality of teeth.

6. The prosthetic implant as defined in claim 2, wherein said ridge being spaced from a peripheral edge of said first or second side wall.

7. The prosthetic implant as defined in claim 1, wherein said top wall including an opening to receive packing material, said packing material including a material selected from the group consisting of medicine, human tissue, animal tissue, synthetic tissue, human cells, animal cells, synthetic cells, and combinations thereof.

8. The prosthetic implant as defined in claim 1, wherein said bottom wall including an opening to receive packing material, said packing material including a material selected from the group consisting of medicine, human tissue, animal tissue, synthetic tissue, human cells, animal cells, synthetic cells, and combinations thereof.

9. The prosthetic implant as defined in claim 1, wherein said top wall having a peripheral edge, at least a portion of said peripheral edge being contoured so as not to be sharp.

10. The prosthetic implant as defined in claim 1, wherein said bottom wall having a peripheral edge, at least a portion of said peripheral edge being contoured so as not to be sharp.

11. The prosthetic implant as defined in claim 1, wherein said top wall being inclined from said second side wall to said first side wall.

12. The prosthetic implant as defined in claim 1, wherein said bottom wall being inclined from said second side wall to said first side wall.

13. The prosthetic implant as defined in claim 1, wherein said incline of said top wall being having a substantially constant slope.

14. The prosthetic implant as defined in claim 1, wherein said bottom wall being inclined from said back end wall to said front end wall.

15. The prosthetic implant as defined in claim 1, wherein said first side wall including an opening to receive packing material, said packing material including a material selected from the group consisting of medicine, human tissue, animal tissue, synthetic tissue, human cells, animal cells, synthetic cells, and combinations thereof.

16. The prosthetic implant as defined in claim 1, wherein said second side wall including an opening to receive packing material, said packing material including a material selected from the group consisting of medicine, human tissue, animal tissue, blood, stem cells and combinations thereof.

17. The prosthetic implant as defined in claim 1, wherein at least one of said front end wall, said back end wall, said first side wall and said second side wall including an opening, said opening adapted to receive an instrument to guide said prosthetic implant between adjoining vertebrae in a spinal column, to receive an implant to secure said cage in position relative to said vertebrae, and combinations thereof.

18. The prosthetic implant as defined in claim 1, wherein said first side wall being a substantially uniform arcuate surface.

19. A prosthetic implant to form a rigid structure between adjoining vertebrae in a spinal column comprising a cage defined by top, bottom, front end, back end, first side and second side walls, said first and second side wall extending substantially along a longitudinal axis of said cage, said front and back end walls having a width that is less than the length of said first side and said second side walls, said top wall and said bottom wall positionable between and engageable with a surface of an adjacent vertebrae, at least one of said top and bottom walls being inclined downwardly from said second side wall to said first side wall such that at least a portion of said second side wall has a height greater than a height of at least a portion of said first side wall.

20. The prosthetic implant as defined in claim 19, wherein both said top and bottom walls being inclined from said second side wall to said first side wall.

21. The prosthetic implant as defined in claim 19, wherein said second side wall being higher that said first side wall.

22. The prosthetic implant as defined in claim 19, wherein said top and bottom walls include a plurality of ridges to engage a surface of an adjacent vertebrae.

23. The prosthetic implant as defined in claim 22, wherein said ridges include a plurality of teeth.

24. The prosthetic implant as defined in claim 19, wherein said ridges are spaced from a peripheral edge of said first and second side wall.

25. The prosthetic implant as defined in claim 19, wherein said top and bottom walls include an opening to receive packing material, said packing material including a material selected from the group consisting of medicine, human tissue, animal tissue, synthetic tissue, human cells, animal cells, synthetic cells, and combinations thereof.

26. The prosthetic implant as defined in claim 19, wherein said top, bottom, front end, back end, first side and second side walls each having a peripheral edge, at least a portion of said peripheral edges of each of said walls being contoured so as not to be sharp.

27. The prosthetic implant as defined in claim 19, wherein said top and bottom walls are inclined from said back end wall to said front end wall.

28. The prosthetic implant as defined in claim 19, wherein said back side wall being higher than said front side wall.

29. The prosthetic implant as defined in claim 19, wherein at least one of said front end wall, said back end wall, said first side wall and said second side wall including an opening, said opening adapted to receive an instrument to guide said prosthetic implant between adjoining vertebrae in a spinal column, to receive an implant to secure said cage in position relative to said vertebrae, and combinations thereof.

30. The prosthetic implant as defined in claim 29, including a cavity within said cage, said cavity in communication with said at least one of said opening in at least one of said front end, said back end, said first side and said second side walls, said cavity adapted to receive packing material that includes a material selected from the group consisting of medicine, human tissue, animal tissue, synthetic tissue, human cells, animal cells, synthetic cells, and combinations thereof.

31. The prosthetic implant as defined in claim 19, wherein said front side wall having a substantially uniform arcuate surface.

32. A prosthetic implant to form a rigid structure between adjoining vertebrae in a spinal column comprising a cage defined by top, bottom, front end, back end, first side and second side walls, said first and second side walls extending substantially along a longitudinal axis of said cage, said front and back end walls having a width less than the length of said first side and said second side walls, said top wall and said bottom wall positionable between and engageable with a surface of an adjacent vertebrae, said first side wall having an arcuate surface, at least one of said top and bottom walls being inclined downwardly from said back end wall to said front end wall such that at least a portion of said back end wall has a height greater than a height of at least a portion of said front end wall, at least one of said top and bottom walls being inclined downwardly from said second side wall to said first side wall such that at least a portion of said second side wall has a height greater than a height of at least a portion of said first side wall.

33. The prosthetic implant as defined in claim 32, wherein said top wall includes a plurality of ridges to engage a surface of an adjacent vertebrae, at least one of said ridge includes a plurality of teeth.

34. The prosthetic implant as defined in claim 32, wherein said bottom wall includes a plurality of ridges to engage a surface of an adjacent vertebrae, at least one of said ridge includes a plurality of teeth.

35. The prosthetic implant as defined in claim 33, wherein said top wall includes a plurality of ridges to engage a surface of an adjacent vertebrae, at least one of said ridge includes a plurality of teeth.

36. The prosthetic implant as defined in claim 35, wherein said plurality of ridges are spaced from a peripheral edge of said first and second side wall.

37. The prosthetic implant as defined in claim 32, wherein said top wall and said bottom being inclined from said second side wall to said first side wall.

38. The prosthetic implant as defined in claim 32, wherein incline of said top wall from said second side wall to said first side wall having a substantially constant slope.

39. The prosthetic implant as defined in claim 32, in incline of said bottom wall from said second side wall to said first side wall having a substantially constant slope.

40. The prosthetic implant as defined in claim 37, wherein incline of said top wall and said bottom wall from said second side wall to said first side wall having a substantially constant slope.

41. The prosthetic implant as defined in claim 32, wherein said top wall and said bottom being inclined from said back end wall to said front end wall.

42. The prosthetic implant as defined in claim 40, wherein said top wall and said bottom being inclined from said back end wall to said front end wall.

43. The prosthetic implant as defined in claim 32, wherein incline of said top wall from said back end wall to said front end wall having a substantially constant slope.

44. The prosthetic implant as defined in claim 32, wherein incline of said bottom wall from said back end wall to said front end wall having a substantially constant slope.

45. The prosthetic implant as defined in claim 41, wherein incline of said top wall and said bottom wall from said back end wall to said front end wall having a substantially constant slope.

46. The prosthetic implant as defined in claim 42, wherein incline of said top wall and said bottom wall from said back end wall to said front end wall having a substantially constant slope.

47. The prosthetic implant as defined in claim 32, wherein said top wall including an opening to receive packing material, said packing material including a material selected from the group consisting of medicine, human tissue, animal tissue, synthetic tissue, human cells, animal cells, synthetic cells, and combinations thereof.

48. The prosthetic implant as defined in claim 32, wherein said bottom wall including an opening to receive packing material, said packing material including a material selected from the group consisting of medicine, human tissue, animal tissue, synthetic tissue, human cells, animal cells, synthetic cells, and combinations thereof.

49. The prosthetic implant as defined in claim 32, wherein said first side wall including an opening to receive packing material, said packing material including a material selected from the group consisting of medicine, human tissue, animal tissue, synthetic tissue, human cells, animal cells, synthetic cells, and combinations thereof.

50. The prosthetic implant as defined in claim 32, wherein said second side wall including an opening to receive packing material, said packing material including a material selected from the group consisting of medicine, human tissue, animal tissue, blood, stem cells and combinations thereof.

51. The prosthetic implant as defined in claim 32, wherein said top, bottom, front end, back end, first side and second side walls each having a peripheral edge, at least a portion of said peripheral edges of each of said walls being contoured so as not to be sharp.

52. The prosthetic implant as defined in claim 32, wherein at least one of said front end wall, said back end wall, said first side wall and said second side wall including an opening, said opening adapted to receive an instrument to guide said prosthetic implant between adjoining vertebrae in a spinal column, to receive an implant to secure said cage in position relative to said vertebrae, and combinations thereof.

53. The prosthetic implant as defined in claim 32, wherein said first side wall being a substantially uniform arcuate surface.

54. The prosthetic implant as defined in claim 32, wherein said second side wall being a substantially planar surface.

55. The prosthetic implant as defined in claim 53, wherein said second side wall being a substantially planar surface.

56. The prosthetic implant as defined in claim 46, wherein said first side wall being a substantially uniform arcuate surface.

57. The prosthetic implant as defined in claim 56, wherein said second side wall being a substantially planar surface.

58. The prosthetic implant as defined in claim 32, wherein said top, bottom, front end, back end, first side and second side walls each having a peripheral edge, at least a portion of said peripheral edges of each of said walls being contoured so as not to be sharp.

59. The prosthetic implant as defined in claim 58, wherein said top wall includes a plurality of ridges to engage a surface of an adjacent vertebrae, at least one of said ridge includes a plurality of teeth.

* * * * *